United States Patent [19]
Miller et al.

[11] Patent Number: 6,017,715
[45] Date of Patent: *Jan. 25, 2000

[54] METHOD FOR DETERMINING THE TOXICITY OF SELECTED ORGANIC CHEMICALS IN AN AQUEOUS SAMPLE MATRIX USING ANTIBODY-MEDIATED SELECTIVE REMOVAL PROCESSES

[76] Inventors: Jeffrey L. Miller; Micheal J. Miller, both of c/o AQUA-Science, 17 Arboretum Dr., Davis, Calif. 95616

[ * ] Notice: This patent issued on a continued prosecution application filed under 37 CFR 1.53(d), and is subject to the twenty year patent term provisions of 35 U.S.C. 154(a)(2).

[21] Appl. No.: 08/708,770

[22] Filed: Sep. 5, 1996

[51] Int. Cl.[7] .................. G01N 33/53; G01N 33/543; G01N 33/551; G01N 33/546

[52] U.S. Cl. ................... 435/7.1; 435/962; 436/518; 436/523; 436/524; 436/526; 436/531; 436/534; 436/824

[58] Field of Search ............... 435/7.1, 962; 436/518, 436/523, 524, 526, 531, 534, 824

[56] References Cited

U.S. PATENT DOCUMENTS 5,518,890  5/1996  Starkweather et al. .................. 436/526

OTHER PUBLICATIONS

Lawruk et al., "Determination of Chlorothalonil in Water and Agricultural Products by a Magnetic Particle–Based Enzyme Immunoassay," *Journal of Agricultural and Food Chemistry,* vol. 43, pp. 1413–1419 (May 1995).

Kaufman et al., "Immunoassay of pesticides: an update," *Journal of AOAC International,* vol. 78, No. 4, pp. 1079–1090, (Jul.–Aug. 1995).

Herzog et al., "Immunochemical measurement of chlorpyrifos in multiple matrices," *Journal of Clinical Ligand Assay,* vol. 18, No. 3, pp. 150–155 (1995).

*Primary Examiner*—James C. Housel
*Assistant Examiner*—Rodney P. Swartz
*Attorney, Agent, or Firm*—Christopher L. Stone

[57] ABSTRACT

A method for identifying a toxicant in an environmental water or soil sample comprising (a) adding to the sample an antibody known to form a complex with a toxicant suspected to be present in the sample; (b) incubating the antibody with the sample for a time and under conditions sufficient to allow complexes to form between the antibody and the toxicant; and (c) comparing the toxicity of the sample treated as in the step (b) with the toxicity of the sample prior to the step (a), whereby a reduced amount of toxicity of the treated sample compared with the untreated sample indicates the presence of the toxicant in said sample. The method described herein provides unexpected and important advantages by providing more accurate correlations between predicted and observed toxicity of a sample than previous methods.

12 Claims, 4 Drawing Sheets

METHOD FOR DETERMINING THE TOXICITY OF SELECTED ORGANIC CHEMICALS IN AN AQUEOUS SAMPLE MATRIX USING ANTIBODY-MEDIATED SELECTIVE REMOVAL PROCESSES

BACKGROUND OF THE INVENTION

1. Field of the Invention

The invention is directed to a novel method of identifying toxicants in a sample. More particularly, the invention relates to a method of selectively determining the identity and the actual toxicity of toxicants in an aqueous matrix of water, wastewater or soil using antibodies.

2. State of the Art

The discharge of chemicals into the aquatic environment can result in measurable toxicity to aquatic organisms residing in the water column and/or aqueous sediments. These discharges are regulated by various state or federal agencies, which may require the discharger to perform testing to assure that the discharges are not causing toxicity to the aquatic environment. Accordingly, increased attention has been focused on methods of identifying the causes of toxicity in water subject to industrial and agricultural runoff to enable appropriate measures to be taken to control the source of the toxicant. These methods use a variety of approaches to separate toxic samples into different fractions and/or eliminate toxicity due to specific classes of chemicals.

In recent years, increased emphasis has been placed on the use of a standardized set of guidelines for determining the identity of toxicants in a water sample. The United States Environmental Protection Agency has produced a series of documents that address analysis of sources of chronic and acute toxicity, referred to as Toxicity Identification Evaluations ("TIE's") (see e.g., May 1992 EPA Publication, Technical Report 02-92; September 1993 EPA Publication, Technical Report 01-93; September 1993 EPA Publication, Technical Report 02-93). The TIE's utilize a three phase system, which is generally based on the concept of first testing an effluent in a bioassay for toxicity, subsequently separating out specific chemical constituents through either general chemical class separations or specific chemical separations, and retesting the sample to determine if the toxicity was eliminated due to the specific manipulation effected.

Phase I involves characterizing the general chemical classification of the chemical toxicant, e.g., oxidants, ammonia, volatile materials, polar or non-polar organic materials or cationic metals. The Phase I methods employ a series of chemical manipulations which are designed to remove or sequester materials belonging to one or more of the chemical classes described above or render them non-toxic. These manipulations include specific chemical and separative methodologies with a subsequent determination of whether a specific treatment has eliminated the toxicity of the sample. For example, EDTA and sodium thiosulfate additions, a graduated pH test, aeration and filtration manipulations, and the use of C-18 solid phase extraction (SPE) resin columns are generally used for Phase I categorizations.

Phase II is directed in determining the identity of the specific chemicals which have a role in the toxicity of the sample. In the September 1993 EPA Publication, Technical Report 01-93, the identification of toxicity due to organic chemicals is delineated in a multi-step process. First, the organics in the effluent sample are chemically separated according to their physical-chemical characteristics, generally by passing the effluent sample through a resin column which is sequentially eluted with an organic solvent or mixture of solvents into a series of fractions. Each fraction is then bioassayed and the fractions which continue to produce toxicity in the bioassay organisms are retained for further testing. Additional characterization of the toxic fractions is performed by combining and concentrating the toxic fractions on a resin column and subjecting this concentrate to additional fractionation using advanced analytical instrumentation, such as high performance liquid chromatography (HPLC). The individual fractions obtained by this process are bioassayed and those which produce toxicity are subjected to analysis by gas chromatography (GC), GC mass spectrophotometry (GC/MS) and/or HPLC/MS. If metals are indicated as being responsible for toxicity in the Phase I testing, e.g., with EDTA or similar chelator testing, then further analysis of these toxicants is necessary. The September 1993 EPA publication indicates that suitable testing procedures for the presence of cationic elements include the use of advanced instrumentation, such as atomic absorption analysis, inductively-coupled plasma-atomic emission spectroscopy, and inductively-coupled plasma-mass spectrophotometry.

The Phase III TIE process is essentially the same for both organic and metal toxicants. The overall goal of this phase is to determine if the candidate toxicant(s) identified in Phase I and 11 quantitatively account for the toxicity observed in the sample. The process consists of comparing the toxicity of the effluent sample with the candidate toxicants. In practice, this is accomplished by (1) measuring the level of toxicity in the sample, (2) measuring the level of each of the candidate toxicants in the sample, (3) measuring the toxicity of the candidate toxicants in "clean water", e.g., high purity water amended with appropriate salts to attain specifications for EPA Moderately Hard Water, or in a synthetic matrix similar to that of the sample and (4) summing the total toxicity of the candidate toxicants and comparing that with the total toxicity of the sample. If the values closely agree, the conclusion is that the candidate toxicants account for the toxicity of the sample.

These TIE testing methods have been found useful in many instances for determining the toxicity of a sample. In fact, when the Phase I and Phase II process is conducted in a technically competent manner, the results may often lead to the identity of one or more candidate toxicants. However, the methods utilized in the TIE Phase III process for the identification of specific organic non-polar toxicants and metal toxicants have several drawbacks.

One disadvantage of the present system is that there are many naturally-occurring substances in environmental samples which interact with toxicants to render a portion of the chemical toxicant biologically unavailable. Thus, comparing the concentrations of chemicals which cause toxicity in "clean water" with measured concentrations of the chemicals in environmental samples typically results in substantially more toxicity being predicted (based on measured chemical concentrations) than is actually measured by bioassay of the sample. This leads to erroneous results regarding the toxic components of the sample and, accordingly, the possibility of unnecessary or improperly calculated remedial measures taken to correct the problem.

Another disadvantage of present systems is that the analytical procedure used to identify candidate toxicants in a sample may not provide the required level of sensitivity to reliably detect the chemicals of interest in the sample matrix. For example, the level of accuracy and precision associated with procedures such as HPLC, GC and MS varies considerably due to the nature of the particular toxicant, the level of toxicant in the sample and the complexity of the sample matrix.

Another disadvantage of present systems is that specific toxicants may be lost during sample manipulation due to adsorption (i.e., onto resin columns), volatility and release of toxicant resulting in incomplete recovery of toxicant. Attempts to remedy such problems include estimating the amount of toxicant lost during the manipulations. However, these estimations are subject to error which can effect the results of the analysis.

Another disadvantage of present systems is their inefficiency in identifying additive, synergistic or antagonistic interaction effects caused by the presence of multiple toxicants in the sample. The inability of the prior art systems to identify such effects is due to the necessity of destroying the integrity of the sample itself in order to remove one or several toxicants. Using the prior art systems, it is not generally possible to obtain an accurate assessment of the actual toxicity contributed by a specific toxicant because the available methods do not permit selective removal of the specific toxicant without unintentional partial removal of other materials (other chemical toxicants and/or other components of the sample matrix). Accordingly, it is not possible to effect a direct comparison between the lethality caused by the toxicant alone at a concentration equivalent to that in the original sample or to determine if there is an interactive effect between multiple constituents of the sample.

Another disadvantage of present systems is that they may unintentionally and unknowingly add toxic materials to the sample matrix during the manipulations of Phase I and Phase II, resulting in false results.

Another disadvantage of present systems is that costly and intricate instrumentation is necessary to carry out the tests.

In contrast with the prior art systems described above, the present invention provides a novel method for the measurement of the toxicity of an environmental sample which avoids the above disadvantages. Importantly and surprisingly, Applicants method described herein overcomes the problems of the prior art by providing a highly sensitive and accurate system which properly assigns toxicity to various chemical components.

SUMMARY OF THE INVENTION

It is an object of the invention to provide a method for quickly and accurately identifying the toxicity of a selected chemical toxicant in an aqueous matrix.

It is a further object of the invention to provide for a method of making a determination of the identity of a toxicant without problems caused by loss of original toxicants in a sample or addition of toxicants from manipulations.

It is yet another object of the invention to provide a method which enables the determination of toxic effects caused by quantities of toxicant which are too minute to be detected through advanced analytical detection instrumentation such as HPLC, GC and MS.

It is still a further object of the invention to provide a method of determining additive, synergistic and/or antagonistic interaction effects of multiple toxicants in a sample.

According to the invention, a method is provided for identifying a toxicant in a sample comprising: (a) adding to the sample an antibody known to form a complex with a toxicant suspected to be present in said sample; (b) incubating the antibody with the sample for a time and under conditions sufficient to allow complexes to form between the antibody and the toxicant; and (c) comparing the toxicity of the sample treated as in step (b) with the toxicity of the sample prior to step (a), whereby a reduced amount of toxicity of said treated sample compared with said untreated sample indicates the presence of the toxicant in said sample. Preferably, the antibody/toxicant complex is removed from the sample prior to step (c). More preferably, the antibody is associated with a bead or particle which, by removal of the bead or particle, permits removal of both formed antibody/toxicant complexes and uncomplexed antibody prior to comparing the toxicity as in step (c).

The present invention has the advantage of allowing a rapid determination of the identity and interactive effects of toxicants present in a given environment through simple testing in the laboratory without extensive, complex and expensive instrumentation. This determination provides an additional advantage over prior art methods in that the degree of toxicity caused by certain chemical and their respective bioavailability is accurately determined making the design of remedial measures more accurate.

DETAILED DESCRIPTION OF THE INVENTION

"Toxicant" means a chemical or particulate material which causes either chronic or acute toxic effect (e.g., lethality, abnormal development, impaired reproduction, etc.) in a living organism. In determining whether a chemical or material is a toxicant, analysis of whether a toxic effect occurs in at least a portion of a population of organisms subjected to the chemical or particulate material in a bioassay is performed. Common toxicants include chemicals such as dioxin, carbofuran, chlorpyrifos, diazinon or other synthetic or natural toxins which are associated with waste or sewage effluent.

"Acute toxicity" means the toxicity that occurs in a short period of time, operationally defined by a specific time period, generally 96 hours or less.

"Chronic toxicity" means toxicity that occurs as the result of long exposures in which sublethal effects (fertilization, growth, reproduction) are measured in addition to lethality. Measures of chronic toxicity are used to ascertain the effects of long-term exposure to chemicals, waste-waters and leachates to aquatic organisms. True chronic toxicity tests include the life-cycle of the organism.

"Bioassay" means an assay which measures the toxic effect of a sample matrix or an individual chemical in solution. Generally, bioassays are conducted on a microorganism or aquatic species which is either indigenous to the region from which the sample is taken, or on any of a number of well-characterized organisms commonly used in such testing. Suitable organisms for use in a bioassay include cladocerans such as *Ceriodaphnia dubia, Daphnia magna* or *Daphnia pulex,* mysids such as *Neomysis mercedis;* and fish such as the fathead minnow (*Pimephales promelas*).

"Additive interaction" or "additive effect" means that, in a sample containing multiple chemical toxicants, the combination of toxicants produces toxicity in direct relation to the concentration of individual toxicants in the sample.

"Antagonistic interaction" or "antagonistic effect" means that, in a sample containing multiple chemical toxicants, the combination of toxicants produces less toxicity than would be predicted based on the concentration of the individual toxicants in the sample.

"Synergistic interaction" or "synergistic effect" means that, in a sample containing multiple chemical toxicants, the combination of toxicants produces more toxicity than would be predicted based on the concentration of the individual toxicants.

"Sample" means any medium into which toxicants have been introduced. Generally, a sample will be an aqueous solution, slurry, mixture or combination of compositions which is to be subject to toxicology testing. Thus, samples may be derived from rivers, oceans, lakes or estuaries, sediments extracted from the beds or banks of rivers, oceans, lakes or estuaries, agricultural or industrial runoff or any other medium which is known to harbor toxicants which can be analyzed under aqueous conditions. Sample is not limited to compositions which are drawn as aqueous solutions, but should also include any sample which is capable of being suspended in an aqueous solution and effecting a reaction of specific constituents therein with antibody therefor. Thus, ground soil which has been contaminated with toxicants may be used in the present invention by simply suspending the soil in an aqueous medium.

"Sample matrix" or "matrix" means the constituents of a sample which may have an effect on the toxicity of the sample. Many different chemicals may be present in a given sample. Accordingly, a plurality of these chemicals may have an impact on the actual toxicity of the sample by their effect singly or their additive, antagonistic or synergistic interactions with the other constituents of the sample. The overall combination of these effects is due to the specific matrix present in the sample.

According to the present invention, a method is provided for identifying a toxicant in a sample comprising: (a) adding to the sample an antibody known to form a complex with a toxicant suspected to be present in said sample; (b) incubating the antibody with the sample for a time and under conditions sufficient to allow complexes to form between the antibody and the toxicant; and (c) comparing the toxicity of the sample treated as in step (b) with the toxicity of the sample prior to step (a), whereby a reduced amount of toxicity of said treated sample compared with said untreated sample indicates the presence of the toxicant in said sample.

The antibody selected should correspond to a specific toxicant believed to be present in the sample. In selecting the antibody for use, it is necessary to determine or make an assumption regarding the specific chemicals in the sample. Such assumptions are readily made according to established procedures in the art. For example, a suspected toxicant may have been identified pursuant to classifications of chemicals as in the Phase I EPA guidelines described above, or may have been identified through tracking the likely source of waste release. For example, in stormwater and municipal effluent samples, the organophosphate insecticides (OPs), diazinon and chlorpyrifos, have been identified as the causes of toxicity in these sample matrices by Phase I and II TIE Procedures used in this and other laboratories. Once a determination has been made as to a suspected chemical toxicant, an antibody should be selected which is known to be sufficiently specific and reactive with the toxicant so as to form an antibody-toxicant immunocomplex. Suitable antibodies are known to those of skill in the art for a number of chemicals believed to act as toxicants when released into the environment as are methods for their production. Such antibodies include, for example, those reactive with chlorinated dibenzo-p-dioxins described in European Patent Application Publication No. 258 006; agricultural herbicides, including 2-4-D, Silvex, Toxaphene, Paraquat, Diquat, Diuron, Acetochlor, Benomyl, Picloram, Atrazine, Linuron, Molinate, Trichlopyr, and Chlortaluron; agricultural insecticides, including Diazinon, Chlorpyrifos, Aldicarb, Cyclodienes, DDT, Fenitrothion, Methoprene, Carbofuran, Triazines, Azinphos, and Pirimiphos; or other environmental contaminants, such as polynuclear aromatic hydorcarbons, polychorinated biphenyls, and polynuclear terphenyls. Antibodies for various toxicants are further available from Millipore (Envirogard™, Bedford, Mass.), ENSYS (Research Triangle Park, N.C.), and ImmunoSystems Inc. (Scarborough, Me.).

After adding the antibody to the sample, the mixture of antibody and sample should be incubated for a time and under conditions sufficient to allow complexes to form between any toxicant present and the antibody. Such conditions will depend primarily on the specific nature of the antibody and the toxicant suspected to be present. The determination and selection of suitable conditions for a given toxicant-antibody reaction is well within the skill of those of skill in the art.

After the antibody has been added to the sample and the solution allowed to incubate for a time under conditions sufficient to permit antibody-toxicant complexes to form, the antibody/sample mixture is analyzed for toxicity and the toxicity compared with that of the sample prior to the addition of antibody. After formation of the antibody-toxicant complex, the complex is preferably separated out from the sample to eliminate any unforeseen toxic effects caused by the complex. Such separation can be effected by any method known to be useful for the separation of antibody-conjugate complexes, for example, filtration, centrifugation, precipitation, microfiltration, magnetic separation or any similar art-recognized means for separating such complexes.

A preferred method of removing antibody comprises binding, attaching or otherwise associating the antibody for the specific toxicant to an immobilized support prior to adding to the sample. Preferably, the support comprises a glass bead. In this embodiment, the particles are settled and decanted from the sample after the incubation. However, it is contemplated as within the scope of the invention to test the toxicity of the incubated sample with the antibody-toxicant complex present therein. In this embodiment, any toxic effects caused by the complex itself or by the excess unbound antibody in solution should be accounted for. Suitable methods for immobilizing antibodies to such solid supports are provided in, e.g., Dietrich, et al., Food and Agric. Immun., vol. 7, pp. 203–220 (1995), which disclosure is herein incorporated by reference.

Another preferred embodiment comprises using antibodies which are attached or associated with magnetic particles. In this embodiment, the antibodies may be removed from the solution after incubation by simply applying magnetic force to the incubation vessel and decanting the solution minus the antibody-toxicant complexes and excess antibody. A suitable procedure for preparing such magnetic particles is provided in U.S. Pat. No. 5,320,944, which disclosure is herein incorporated by reference.

The toxicity of the incubated sample, either including the antibody/toxicant complex or having the complex removed therefrom, is tested and compared with the toxicity of the original sample. Preferably, the relative toxicity is compared by conducting a bioassay test on both samples. A suitable bioassay test is described in the May 1992 EPA Publication, Technical Report 02-92, at Section 5. However, alternative assays for determining toxicity including those well known in the art may be utilized as appropriate for a given sample or toxicant. By comparing the toxicity of the sample prior to the addition of antibody and that of the sample after addition of antibody, it is possible to determine whether the toxicity of the sample is caused by the specific toxicant believed to be present in the sample, and moreover, to determine how much of the sample's toxicity is due to the specific toxicant.

The above procedure can be repeated with different antibodies specific for different toxicants which may be present in the sample. In this way it is possible to provide a fingerprint of the toxicity of the sample. Similarly, by comparing the results of antibody reactions with different toxicants, it is possible to determine the presence of additive, antagonistic and synergistic effects within the sample.

The invention will be further understood by reference to the following examples, which are intended to illustrate, and not to limit, the invention.

EXAMPLES

Example 1
Calculation of Toxicity Units for Samples

Figure 1:
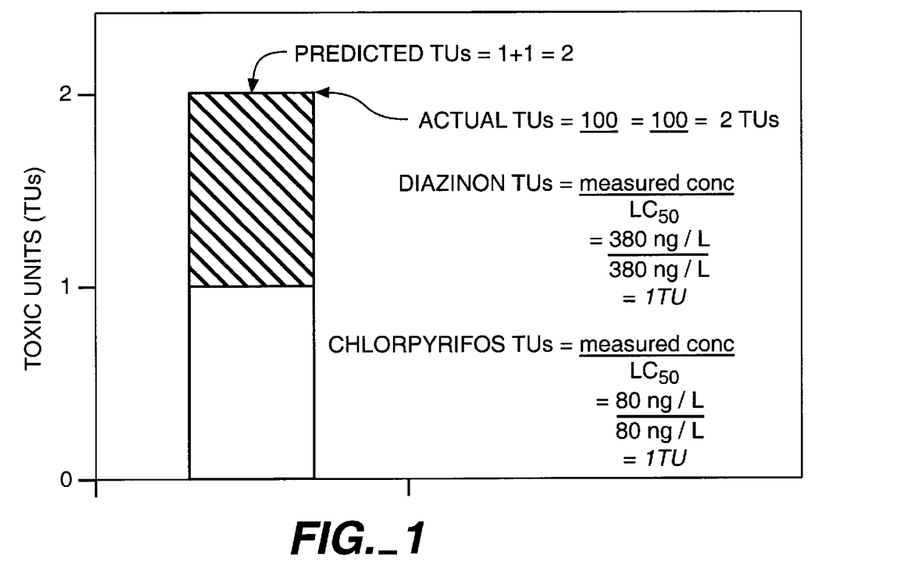
FIG. 1 illustrates the calculation of toxic units for a given sample for diazinon and chlorpyrifos.

The following example illustrates calculation of data used herein to illustrate the effect of antibody-mediated selective removal process. In this example, the sample matrix is laboratory water, which contains 1 Toxic Unit (TU) of chlorpyrifos (80 ng/L) and 1 TU of diazinon (380 ng/L). The TUs for each are calculated as indicated in FIG. 1.

The indicated $LC_{50}$ values (the calculated concentration that produces 50% mortality in the test animals) for chlorpyrifos and diazinon were determined in this laboratory and are the mean values of 10 and 14 separate tests for chlorpyrifos and diazinon, respectively. The predicted TUs for each chemical is depicted by the arrow. As shown in FIG. 1, a total of 2 TUs was predicted since the toxicity of chlorpyrifos (1 TU) and diazinon (1 TU) are directly additive. In this illustrative example, in which the sample matrix is laboratory water, the predicted TUs and actual TUs are equal. However, as shown in Examples 1a, 1b and 1c below (FIGS. 2, 3 and 4, respectively), with environmental samples, the prior art process (EPA Phase III TIE procedures) does not accurately predict the observed toxicity. In these three examples, the amount of error (percent overprediction) associated with the prior art systems is shown above the total predicted TUs bar for each sample.

Figure 2:
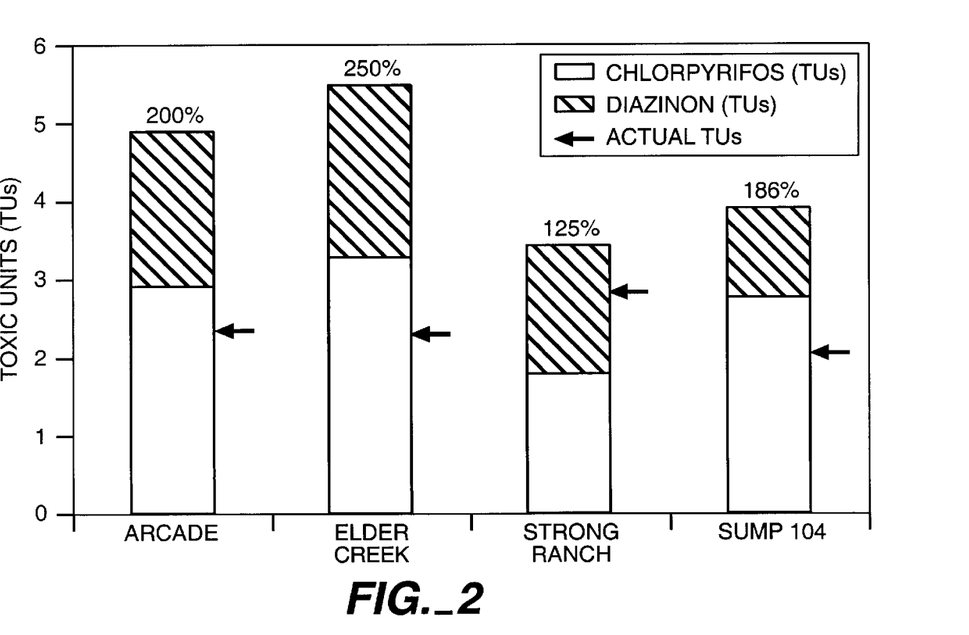
FIG. 2 illustrates the predicted and observed toxicity of stormwater from various northern California locations containing diazinon and chlorpyrifos to Ceriodaphnia.

Example 1a
Predicted and Observed Toxicity of Stormwater From Selected Northern California Sites Containing Diazinon and Chlorpyrifos to Ceriodaphnia In this example, samples from various northern California locations were used to analyze the predicted and observed toxicity of storm water containing diazinon and chlorpyrifos to Ceriodaphnia. As shown in FIG. 2, the prior art system overpredicted the toxicity by an average of 190%.

Figure 3:
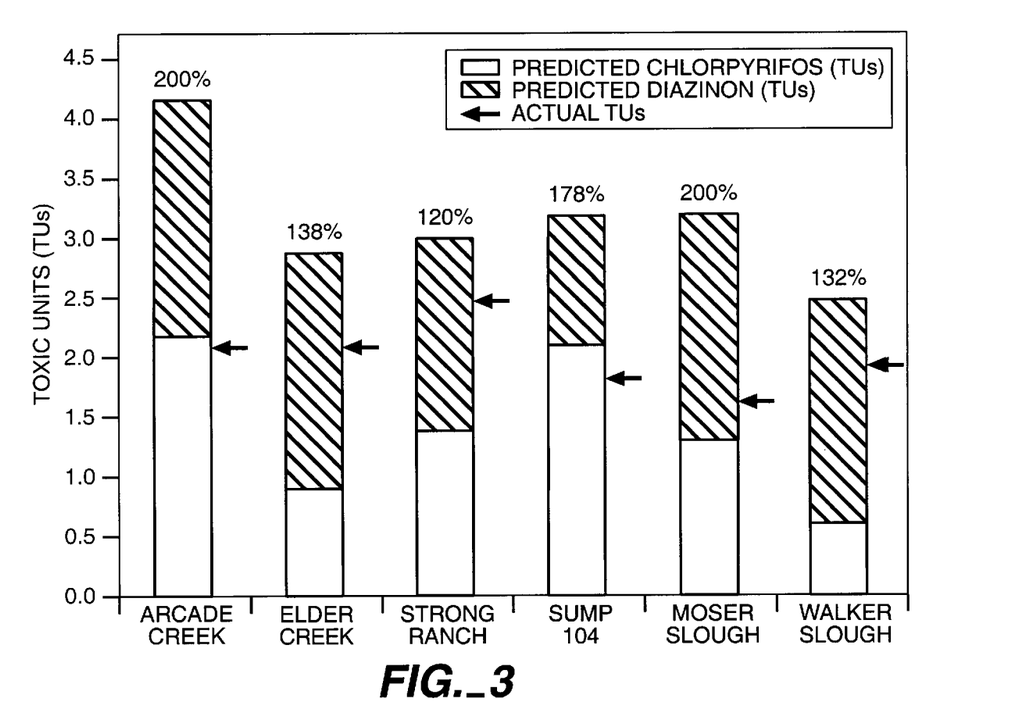
FIG. 3 illustrates the predicted and observed toxicity of stormwater from various northern California locations containing diazinon and chlorpyrifos to Ceriodaphnia.

Example 1b
Predicted and Observed Toxicity of Stormwater From Selected Northern California Sites Containing Diazinon and Chlorpyrifos to Ceriodaphnia In this example, additional samples from various northern California locations were used to analyze the predicted and observed toxicity of storm water containing diazinon and chlorpyrifos to Ceriodaphnia. As shown in FIG. 3, the prior art system overpredicted the toxicity by an average of 161%.

Figure 4:
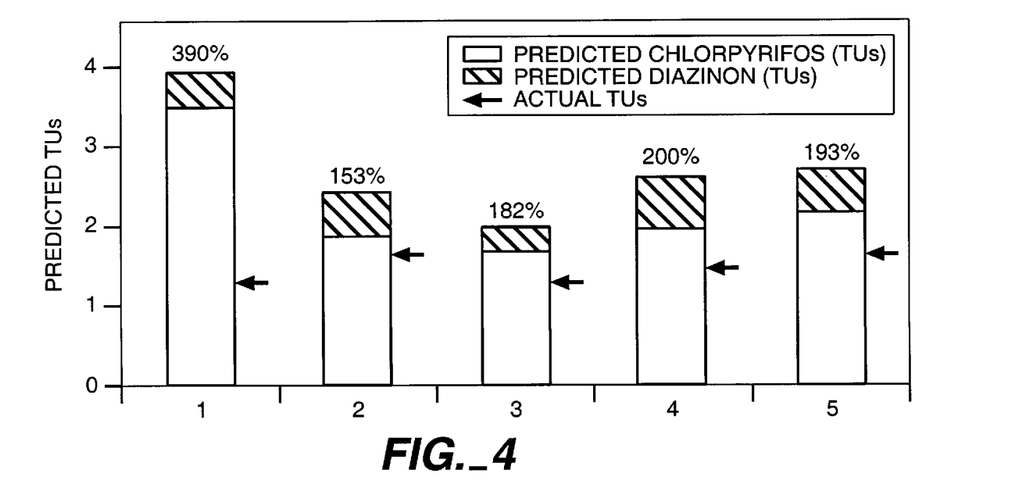
FIG. 4 illustrates the predicted and observed toxicity of municipal effluent from various northern California locations containing diazinon and chlorpyrifos to Ceriodaphnia.

Example 1c
Predicted and Observed Toxicity of Municipal Effluent From Selected Northern California Sites Containing Diazinon and Chlorpyrifos to Ceriodaphnia In this example, samples from various northern California locations were used to analyze the predicted and observed toxicity of municipal effluent containing diazinon and chlorpyrifos to Ceriodaphnia. As shown in FIG. 4, the prior art system overpredicted the toxicity by an average of 224%.

Example 2
Preparation and Functionality Testing of Soluble Antibody

A. Preparation of Purified Soluble Antibody

Rabbit anti-chlorpyrifos IgG (IgG-C) and rabbit anti-trinitrotoluene (IgG-TNT) were purified from serum/glycerol (1:1; v:v) as follows: The serum/glycerol mixture used for long term storage of antibodies was dialyzed against normal saline in an Amicon stirred cell using a 30,000 MW-cutoff membrane to remove the glycerol. To the dialyzed protein solution, an equal volume of 75% saturated solution of ammonium sulfate was added dropwise with stirring to yield a final concentration of 32.5% saturated ammonium sulfate. The mixture was centrifuged at 10,000×g for 20 minutes and the supernatant was discarded. The pellet was washed once with 32.5% saturated ammonium sulfate and then resuspended in 0.014M phosphate, pH 6.0. This was dialyzed extensively against phosphate buffer to remove the ammonium sulfate and then concentrated to <5 mL. This was then loaded on a column of DEAE cellulose which had been pre-equilibrated in phosphate and the fractions containing IgG were collected and pooled. The resultant pooled fraction contained 12–14 mg IgG/mL.

B. Functionality Testing of Purified IgG

An experiment was conducted to determine if purified soluble (free) rabbit anti-chlorpyrifos IgG (IgG-C) could selectively remove the toxicity caused by chlorpyrifos in a solution containing both chlorpyrifos and diazinon. The removal of toxicity would occur if the IgG-C interacted with the chlorpyrifos to render this chemical biologically unavailable to the test organism (Ceriodaphnia). To control for non-specific protein binding by the IgG to the target chemicals, IgG for trinitrotoluene (IgG-TNT) was used. If non-specific protein binding occurred, the measured TUs of the chlorpyrifos and diazinon solution would be substantially less than the predicted TUs. In this test, laboratory water was fortified with 176 ng/L of chlorpyrifos and 617 ng/L of diazinon. The concentrations of diazinon and chlorpyrifos were measured by using a commercially-available enzyme-linked immunosorbant assay (ELISA) analytical kit (Envirogard™, ENSYS, Research Triangle Park, N.C.). The TUs predicted from the concentrations of diazinon and chlorpyrifos and the actual TUs measured by the bioassays in the presence and absence of IgG-C and IgG-TNT were calculated as described in Example 1. The results are shown below in Table 1.

TABLE 1

Effect of Addition of Soluble Antibody on the Toxicity of Diazinon and Chlorpyrifos to Ceriodaphnia (Test 1)

| Sample Description | Predicted TUs[a] | Measured TUs[b] |
|---|---|---|
| Lab Spike: | | |
| Chlorpyrifos (176 ng/L = 2.2 TUs) + Diazinon (617 ng/L = 1.6 TUs) | 3.8 | 3.3 |
| Lab Spike + IgG-TNT[c] | 3.3 | 2.8 |
| Lab Spike + IgG-C[d] | 1.6 | 1.5 |

[a]Predicted TUs (Toxic Units) = OP concentration measured by ELISA divided by $LC_{50}$ value for chlorpyrifos (80 ng/L) or diazinon (380 ng/L). The ELISA values for chlorpyrifos were corrected by applying the results of the standard curve obtained with an analytical standard of chlorpyrifos to those obtained with the standard provided with the ELISA kit.
[b]Measured TUs = 100 divided by the $LC_{50}$ value obtained in the 48-hour bioassay with Ceriodaphnia
[c]IgG-TNT = IgG for TNT (non-specific for diazinon and chlorpyrifos). No effect on the toxicity would be predicted.
[d]IgG-C = IgG specific for chlorpyrifos. After addition of IgG-C, the only toxicity expected is that due to diazinon (1.6 TUs)

Figure 5:
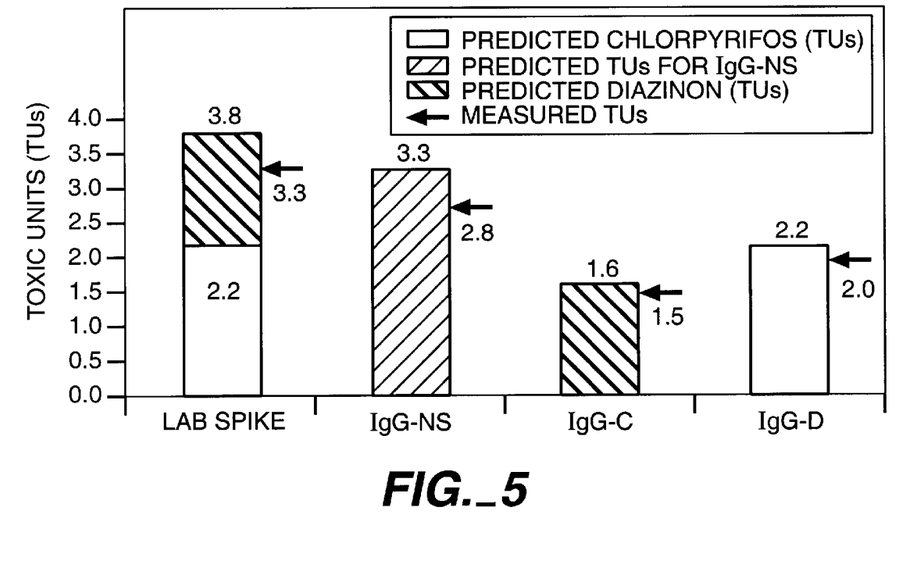
FIG. 5 illustrates the effect of soluble antibody addition on the toxicity of chlorpyrifos and diazinon to Ceriodaphnia.

The bioassay of the mixture produced a total of 3.3 TUs compared to 3.8 toxic units predicted by the concentration of the two OPs. Because this experiment was conducted in high-purity laboratory water, it was expected that the predicted and actual TUs would closely agree since there are no naturally occurring organic materials in the sample matrix to bind with the target chemicals. The protein control treatment (IgG-TNT) produced 2.8 TUs verses 3.3 TUs that was predicted if the IgG-TNT did not remove any of the toxicity from the sample. This result suggests that the protein may have bound to and reduced only a small amount (13%) of the toxicity of either or both of the OPs in the matrix. The IgG-C treatment resulted in 1.6 TUs which compared with 1.6 TUs which was predicted if the treatment removed all the chlorpyrifos and none of the diazinon in the matrix. The IgG-D treatment produced 2.0 TUs compared with 2.2 TUs which was predicted if the treatment removed all the diazinon and none of the chlorpyrifos in the mixture. The results of this study showed that predicted and measured toxicity of the treatments were in close agreement, suggesting that the free IgG-C and IgG-D effectively removed their respective target chemicals without substantially reducing the concentration of the other chemicals in the matrix. This is shown in FIG. 5.

A second experiment was conducted using the free antibody selective removal procedure described above. In this experiment, 150 mL of laboratory dilution water was spiked with 128 ng/L of chlorpyrifos and 836 ng/L of diazinon and treated with IgG-C, IgG-D and IgG-TNT. The predicted TUs and actual TUs are shown in Table 2.

TABLE 2

Effect of Addition of Soluble Antibody on the Toxicity of Diazinon and Chlorpyrifos to Ceriodaphnia (Test 2)

| Sample Description | Predicted Tus[a] | Measured TUs[b] |
|---|---|---|
| Lab Spike: | | |
| Chlorpyrifos (128 ng/L = 1.6 TUs) + Diazinon (646 ng/L = 1.7 TUs) | 3.3 | 3.3 |
| Lab Spike + IgG-TNT[d] | 3.3 | 3.3 |
| Lab Spike + IgG-C[e] | 1.7 | 1.6 |
| Lab Spike − IgG-D[f] | 1.6 | 1.5 |

See Table 1 for footnotes a–d
[e]IgG-D = IgG specific for diazinon. After addition of IgG-C, the only toxicity expected is due to diazinon (1.6 TUs).

Figure 6:
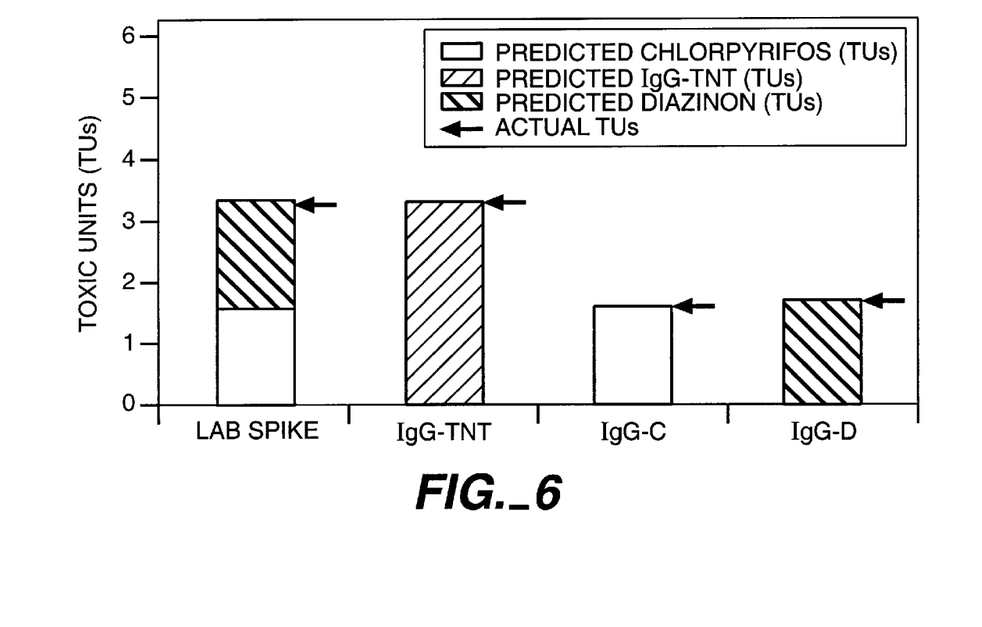
FIG. 6 illustrates the effect of the addition of soluble antibody on the toxicity of diazinon and chlorpyrifos to Ceriodaphnia.

The bioassay produced a total of 3.3 actual TUs, compared with 3.3 TUs that was predicted from the measured concentrations of diazinon and chlorpyrifos. The protein control treatment (IgG-TNT) produced 3.3 actual TUs compared with 3.3 predicted TUs. Treatment with the IgG-C resulted in 1.6 TUs, slightly less than 1.7 TUs predicted if the treatment removed all the chlorpyrifos and none of the diazinon from the solution. Similarly, the IgG-D treatment produced 1.5 TUs, slightly less than 1.7 TUs that was predicted if the treatment removed all the diazinon and none of the chlorpyrifos from the solution. The results are shown in FIG. 6.

Example 3

Selective Removal of Chlorpyrifos From A Matrix Comprising Chlorpyrifos and Diazinon With Immunoaffinity Beads A. Preparation of Immunoaffinity Beads Covalent attachment of antibodies to glass surfaces have been used recently in the development of "biosensors" and other immunoanalytical devices. The technique involves modification of the glass surface with a silane which incorporates a terminal amino group. The method used was based on that used in "Continuous Immunochemical Determination of Pesticides via Flow Injection Immunoanalysis Using Monoclonal Antibodies against Terbutryne Immobilized to Solid Supports". Dietrich, M. and Kramer, P. M. Food and Agricultural Immunology (1985) 7. 203–220. Briefly, the technique involves cleaning of the glass surface with nitric acid followed by derivitization with APTS (3-aminopropyl triethoxy silane). This derivitized surface is then activated with the homobifunctional reagent glutaraldehyde and the IgG molecules are attached via amine groups on the protein.

Pre-derivitized 700A aminopropyl glass beads from Sigma (Cat # G-5019) were used. The beads, as received, were activated by reaction with 6.25% glutaraldehyde solution in 0.01M phosphate buffer, pH 6.0 for 90 minutes followed by extensive washing with the phosphate buffer only. The glass beads were then reacted with IgG solutions overnight. Following the protein coating, the beads were washed extensively with the following: 0.1M phosphate, pH 6.0; 0.1M sodium acetate, pH 4.5, 0.5M NaCl and 0.1M HEPES, pH 8.9; 0.9% NaCl. Following this washing the beads were stored at 4° C. in 0.1M phosphate, pH 6.0, 0.1% BSA, 0.1% sodium azide. Samples of the coating solutions pre- and post-coating were analyzed with the Pierce BCA assay against a rabbit IgG standard for protein content. The initial coating experiment yielded the results shown in Table 3.

TABLE 3

Determination of the Capacity of Glass Beads for IgG

| IgG Type | Activated Beads (mg) | IgG Offered (mg) | Residual IgG (mg) | IgG Loading (mg IgG/gm beads) |
|---|---|---|---|---|
| IgG-C | 0.5 | 0.4 | <0.0625 | >0.675 |
| IgG-C | 0.5 | 0.08 | <0.0625 | >0.035 |
| IgG-C | 0.5 | 4.0 | <0.0625 | >7.88 |

The results of this experiment showed that the beads with the IgG-C antibody at 8 mg IgG/gm beads were not saturated.

Next, the beads were coated at the ratio of 10 mg of IgG-C/gm of beads and again found that there was not detectable protein (<0.0625 mg/mL) in the post-coating solution. This demonstrated that the capacity of the beads exceeded 10 mg IgG-C/gm of beads.

A third attempt to determine the maximal loading capacity of the glass beads involved scaling down the amount of beads used in order to conserve antibody. The results are shown in Table 4.

TABLE 4

Determination of the Capacity of Glass Beads for IgG

| IgG Type | Activated Beads (mg) | IgG Offered (mg) | Residual IgG (mg) | IgG Loading (mg IgG/gm beads) |
|---|---|---|---|---|
| IgG-C | 0.1 | 0.5 | <0.0625 | >4.4 |
| IgG-C | 0.1 | 1.0 | <0.0625 | >8.4 |
| IgG-C | 0.1 | 2.0 | <0.0625 | >19.4 |
| IgG-C | 0.1 | 3.4 | <0.0625 | >33.4 |
| IgG-C | 0.05 | 3.4 | <0.0625 | >66.8 |

This experiment showed that the capacity of the beads was greater than 66.7 mg IgG-C/gm of beads.

Another experiment to define the loading capacity of the beads is summarized in Table 5.

TABLE 5

Determination of the Capacity of Glass Beads for IgG

| IgG Type | Activated Beads (mg) | IgG Offered (mg) | Residual IgG (mg) | IgG Loading (mg IgG/gm beads) |
|---|---|---|---|---|
| IgG-C | 0.02 | 13.6 | 9.8 | 190 |
| IgG-C | 0.02 | 6.8 | 2.8 | 200 |
| IgG-C | 0.02 | 3.4 | 0.65 | 140 |
| IgG-C | 0.02 | 1.7 | <0.0625 | >81.9 |
| IgG-C | 0.02 | 0.85 | <0.0625 | >39.4 |

Based on these results, it appears that the capacity of these beads for rabbit IgG-C is approximately 200 mg IgG-C/gm of glass beads. However, the amount of antibody lost to achieve this maximal loading makes it preferable to load at a lower concentration. All subsequent lots of beads were loaded at a ratio of 100 mg IgG-C/gm of activated beads.

B. Functionality Testing of IgG-Coated Beads (1) Experiments in Laboratory Water An experiment to demonstrate the selective removal of chlorpyrifos by the IgG-C coated beads (100 mg IgG-C/gm of glass beads) were conducted in glass tubes containing 3 mL of laboratory water fortified with 500 ng/L of chlorpyrifos. IgG-C coated beads were added at 10, 50 or 100 mg and the solutions were shaken on an orbital shaker (100 rpm) for 30 minutes. The results are shown in Table 6.

TABLE 6

Removal of Chlorpyrifos from Laboratory Water Using IgG-Coated Glass Beads

| Mg IG-C Beads Used | Initial Chlorpyrifos (ng/L) | Recovered Chlorpyrifos (ng/L) | % Removal |
|---|---|---|---|
| 0 | 500 | 470 | n/a |
| 100 | 500 | <25 | >95 |
| 50 | 500 | <25 | >95 |
| 10 | 500 | 212 | 57.6 |

This experiment showed that 50 mg and 100 mg of the IgG-C-coated beads removed >95% of the chlorpyrifos from laboratory water.

A second experiment was conducted with the IgG-C and IgG-D (diazinon) coated beads. The IgG-D coated beads were prepared as previously described for IgG-C beads. Laboratory water was spiked with chlorpyrifos (176 ng/L) and diazinon (1710 ng/L) and treated with IgG-C, IgG-D or IgG-C+IgG-D. In addition, a treatment control was run concurrently in which the sample was manipulated exactly as with the IgG treatments except no IgG was added to the solution. Aliquots of the spiked solutions were exposed to the IgG for 30 minutes. Concentrations of diazinon and chlorpyrifos were measured by ELISA. The results are shown in Table 7.

TABLE 7

Selective Removal of Chlorpyrifos and Diazinon from Laboratory Water Using IgG-Coated Glass Beads

| Sample Treatment | Chlorpyrifos | | | Diazinon | | | Total | |
|---|---|---|---|---|---|---|---|---|
| | ng/L | % Removal | TUs | ng/L | % Removal | TUs | Predicted TUs | Actual TUs |
| Lab Spike | 176 | n/a | 2.2 | 1710 | — | 4.5 | 6.7 | 6.7 |
| Treatment Control | 175 | 0 | 2.2 | 1482 | 13 | 3.9 | 6.1 | 6.7 |

TABLE 7-continued

Selective Removal of Chlorpyrifos and Diazinon from Laboratory Water
Using IgG-Coated Glass Beads

| Sample Treatment | Chlorpyrifos | | | Diazinon | | | Total | |
|---|---|---|---|---|---|---|---|---|
| | ng/L | % Removal | TUs | ng/L | % Removal | TUs | Predicted TUs | Actual TUs |
| IgG-C | 16 | 94 | 0.2 | 1444 | 16 | 3.8 | 4.0 | 4.3 |
| IgG-D | 194 | 18 | 1.5 | 114 | 93 | 0.3 | 1.8 | 2.0 |
| IgG-C + IgG-D | 16 | 94 | 0.2 | 266 | 84 | 0.7 | 0.9 | 0 |

Figure 7:
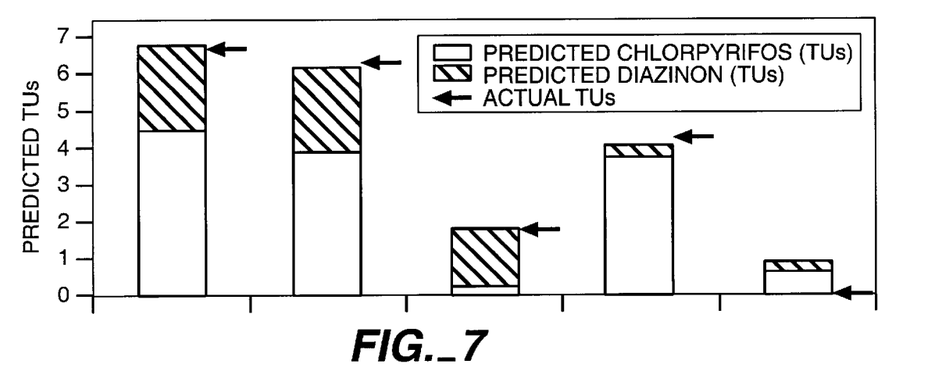
FIG. 7 illustrates the selective removal of chlorpyrifos and diazinon from laboratory water using IgG-coated glass beads.

In this experiment, the predicted and actual TUs for the sample spiked with chlorpyrifos and diazinon were identical (6.7 TUs). Manipulation of the sample without the addition of IgG resulted in little or no change in chlorpyrifos or diazinon concentrations. The IgG-C treatment removed 94% of the chlorpyrifos and 16% of the diazinon, resulting in predicted and measured TUs of 4.0 and 4.3, respectively. The IgG-D treatment removed 93% of the diazinon and 18% of the chlorpyrifos, resulting in predicted and actual TUs of 1.8 and 2.0, respectively. The sequential IgG-C and IgG-D treatments removed 94% and 84% of the chlorpyrifos and diazinon, respectively. This treatment resulted in 0.9 predicted TUs and 0.0 observed TUs. Overall, the IgG coated beads produced high removal (84–94%) of the target chemical with little or no removal (0–18%) of the non-target chemical. The results are shown in FIG. 7.

(2) Experiments with Environmental Samples

An experiment was conducted using IgG-coated beads to demonstrate the selective removal process with an environmental sample. The test sample was a sample of storm water collected from an urban creek near Sacramento, Calif. The sample contained 257 ng/L of chlorpyrifos (3.2 TUs) and 720 ng/L of diazinon (1.9 TUs) by ELISA as shown below:

Predicted TUs $$\text{Diazinon } TUs\ (TU_D):\ \frac{720\ \text{ng/L}}{380\ \text{ng/L}} = 1.9\ TUs$$

$$\text{Chlorpyrifos } TUs\ (TU_c):\ \frac{257\ \text{ng/L}}{80\ \text{ng/L}} = 3.2\ TUs$$

Total TUs: 5.1 TUs

The sample was treated with IgG-C, IgG-D, IgG-C+IgG-D, and with piperonyl butoxide, a chemical reagent which prevents the toxicity of organophosphate insecticides, such as chlorpyrifos and diazinon. The results of these treatments are shown below:

| Bioassay Results | |
|---|---|
| Actual Sample TUs | 2.4 |
| Sample TUs after IgG-C | 1.9 |
| Sample TUs after IgG-D | 1.5 |
| Sample TUs after IgG-C + IgG-D | 1.0 |
| Sample TUs after PB treatment | ~1.0 |

The actual toxicity contributed to the sample can be determined as previously described by measuring the initial toxicity of the sample and treating the sample with the IgG specific for the target chemical. The calculations which indicate the actual toxicity due to chlorpyrifos, diazinon and the "residual" toxicants in the sample are shown below:

| | |
|---|---|
| Actual Sample TUs ($TU_A$): = | 2.4 |
| TUs After IgG Treatments: | |
| Chlorpyrifos TUs = | 0.5 |
| 2.4 $TU_A$ - 1.9 $TU_{IgG-C}$ | |
| Diazinon TUs = | 0.9 |
| 2.4 $TU_A$ - 1.5 $TU_{IgG-D}$ | |
| Residual TUs (after PB Treatment) = | 1.0 |
| 2.4 $TU_A$ - 1.4 $TU_{IgG-C+IgG-D}$ | |
| Total TUs = | 2.4 |

Figure 8:
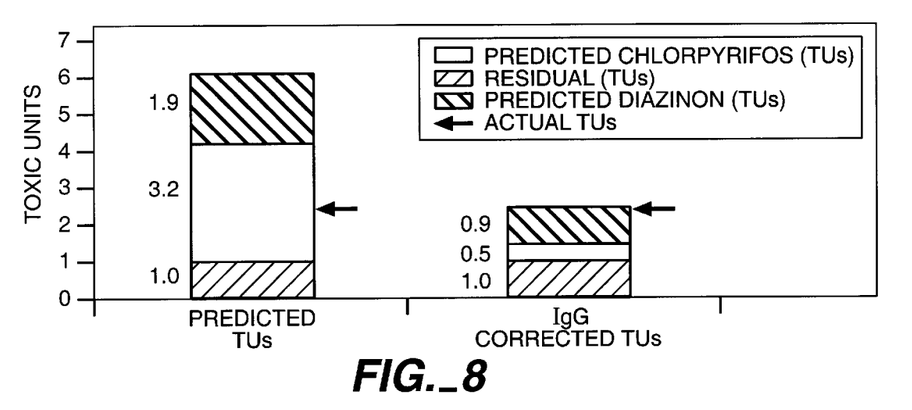
FIG. 8 illustrates the comparison of actual and predicted toxic units using prior art and the method described herein.

Note in this sample that the IgG treatments correctly identify the actual toxicity due to chlorpyrifos (0.5 TUS), diazinon (0.9 TUs) and the residual toxicants (1.0 TUs). The results are shown graphically in FIG. 8.

(3) Determination of Apparent Bioavailability Factor (ABF) Using Antibody-Mediated Selective Removal Procedures As demonstrated in Example 3(B)(2) above, the antibody-mediated selective removal process removes the portion of the target chemical in the sample matrix which is responsible for the toxicity. This form of the chemical, which is soluble or bound to very small particulate or colloid materials, is available for transport by passive (diffusion) or energy-requiring processes (active transport). The antibody-mediated selective removal process can be used to calculate the apparent bioavailability factor (ABF) which is the fraction of the total target chemical in the sample matrix that is available to produce toxicity. Using the data from Example 3(B)(2), the following calculation shows the proportion of the total amount of diazinon and chlorpyrifos in the stormwater sample matrix (as measured by ELISA) which is bioavailable.

TABLE 8

Calculation of Apparent Bioavailability Factor (ABF)

$$\text{ABF for diazinon} = \frac{\text{TUs after treatment with IgG-D}}{\text{TUs predicted}} = \frac{0.9}{1.9} = 0.47$$

$$\text{ABF for chlorpyrifos} = \frac{\text{TUs after treatment with IgG-C}}{\text{TUs predicted}} = \frac{0.5}{3.2} = 0.16$$

Figure 9:
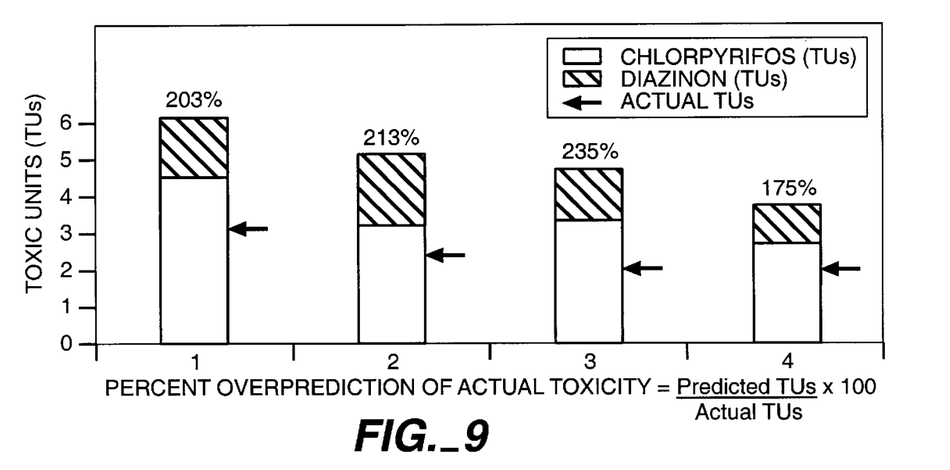
FIG. 9 illustrates the actual and predicted toxicity of a stormwater sample containing diazinon and chlorpyrifos.

As shown above, the bioavailable portion of the total diazinon and chlorpyrifos in the sample was 0.47 (47%) and 0.16 (16%), respectively. To assess if the ABF calculation is a robust estimate of bioavailability of the target chemicals in the sample matrix, the following experiment was performed. An aliquot of the stormwater sample from Example 3(B)(2), was treated with IgG-C and IgG-D to remove the bioavailable fraction of these target chemicals. These treated fractions were then added back to the untreated sample at various ratios to make three subsamples containing varying amounts of chlorpyrifos and diazinon. The original sample and the three treated subsamples were analyzed by ELISA to determine concentrations of the two chemicals and all samples were bioassayed as previously described. The actual and predicted toxicity of the samples are shown in FIG. 9.

The prior art system overpredicted the actual toxicity of the four samples by an average of 207%. Note that this degree of overprediction of toxicity is similar to that observed with other stormwater samples (Examples 1–2) and effluent samples (Example 3) previously described. If the ABF calculation procedure provides a robust estimate of bioavailability, then the ABFs calculated in Table 8 applied to these subsamples should accurately predict the toxicity of these samples, since nothing in the sample matrix has been altered other than the concentrations of the target chemicals. The results are shown in Table 9 below.

TABLE 9

Comparison of Predicted TUs and ABF Corrected TUs with Actual TUs in an Environmental Sample[a]

| Target Chemical | Sample No. | | | |
|---|---|---|---|---|
| | 1 | 2 | 3 | 4 |
| Chlorpyrifos | | | | |
| Predicted TUs | 4.5 | 3.2 | 3.3 | 2.7 |
| ABF Corrected Tus[b] | 0.72 | 0.52 | 0.53 | 0.43 |
| Diazinon | | | | |
| Predicted TUs | 1.6 | 1.9 | 1.4 | 1.0 |
| ABF Corrected TUs[c] | 0.75 | 0.89 | 0.66 | 0.47 |
| Total Predicted TUs | 6.1 | 5.1 | 4.7 | 3.7 |
| Total ABF Corrected TUs | 2.5 | 2.4 | 2.2 | 1.9 |
| Actual TUs | 3.0 | 2.4 | 2.0 | 2.0 |
| Difference[d] | 17 | 0 | 9 | 5 |

[a]Sacramento stormwater sample collected on 4/19/96
[b]ABF corrected chlorpyrifos TUs = predicted chlorpyrifos TUs × calculated ABF (0.16 see table) + residual TUs (1.0)
[c]ABF corrected diazinon TUs = predicted chlorpyrifos TUs × calculated ABF (0.47 see table) + residual TUs (1.0)
[d]Difference = actual TUs − total ABF corrected TUs × 100 actual TUs As shown in Table 9 above, the ABF corrected TUs agreed closely (range=0–19%, mean=8%) with the actual TUs measured in the sample. These data indicate that the ABF values calculated for the environmental sample can be used to accurately predict the observed toxicity in environmental samples. Application of the antibody-mediated selective removal process to this environmental sample demonstrates the utility of this procedure in determining the actual proportion of the target chemical in the sample matrix which is bioavailable. Since all environmental samples contain varying amounts of naturally-occurring organic substances, it is likely that each environmental sample will require testing with IgG-coated beads to determine the ABF.

The method of the invention herein described constitutes a preferred embodiment of the invention. However, it is to be understood that modifications may be made therein without departing from the spirit and scope of the invention, which is described in the following claims.

I claim:

1. A method for determining the contribution to the toxicity of a sample from a toxicant in said sample consisting essentially of:

(a) adding to said sample an antibody known to form a complex with said toxicant suspected to be present in said sample;

(b) incubating said antibody with said sample for a time and under conditions sufficient to allow complexes to form between said antibody and said toxicant; and (c) comparing the toxicity of the sample treated as in said step (b) with the toxicity of the sample prior to said step (a), whereby a reduced amount of toxicity of said treated sample compared with said untreated sample indicates the presence and contribution to the toxicity of the sample by said toxicant.

2. The method according to claim 1, wherein said sample contains more than one toxicant.

3. The method according to claim 2, wherein said more than one toxicant interact in an additive, antagonistic or synergistic manner.

4. The method according to claim 1, further comprising removing said complexes between said antibody and said toxicant from the sample prior to step (c).

5. The method according to claim 1, wherein said toxicant comprises diazinon, chlorpyrifos, carbofuran, 2-4-D, Silvex, Toxaphene, Paraquat, Diquat, Diuron, Acetochlor, Benomyl, Picloram, Atrazine, Linuron, Molinate, Trichlopyr, and Chlortaluron Diazinon, Chlorpyrifos, Aldicarb, Cyclodienes, DDT, Fenitrothion, Methoprene, Carbofuran, Triazines, Azinphos, and Pirimiphos, polynuclear aromatic hydrocarbons, polychorinated biphenyls, polynuclear terphenyls or mixtures thereof.

6. The method according to claim 1, wherein said sample is an aqueous solution.

7. The method according to claim 1, wherein said sample is obtained from a lake, river, ocean or estuary.

8. The method according to claim 1, wherein said sample comprises sediments obtained from a bed or bank of a lake, river, ocean or estuary.

9. The method according to claim 1, wherein said antibody is bound to a solid support comprising glass, polystyrene, or resin particles.

10. A method for determining the contribution to the toxicity of a sample from a toxicant in said sample consisting essentially of:

(a) adding to said sample an antibody known to form a complex with said toxicant suspected to be present in said sample;

(b) incubating said antibody with said sample for a time and under conditions sufficient to allow complexes to form between said antibody and said toxicant;

(c) separating said complexes within said sample or removing said complexes from said sample; and (d) comparing the toxicity of the sample treated as in said steps (b) and (c) with the toxicity of the sample prior to said step (a), whereby a reduced amount of toxicity of said treated sample compared with said untreated sample indicates the presence and contribution to the toxicity of the sample by said toxicant.

11. The method according to claim 10, wherein said antibody is bound to a solid support comprising glass, polystyrene or resin particles.

12. The method according to claim 10, wherein said antibody is removed from said sample by filtration, centrifugation, precipitation or microfiltration.

* * * * *